United States Patent
Van De Wijdeven

[11] Patent Number: 6,001,385
[45] Date of Patent: Dec. 14, 1999

[54] USE OF STARCH FOR TRANSDERMAL APPLICATIONS

[76] Inventor: Giisbertus G. P. Van De Wijdeven, Winde 11, 8265 ED Kampen, Netherlands

[21] Appl. No.: 08/809,096
[22] PCT Filed: Sep. 20, 1995
[86] PCT No.: PCT/NL95/00313
  § 371 Date: Jun. 30, 1997
  § 102(e) Date: Jun. 30, 1997
[87] PCT Pub. No.: WO96/09070
  PCT Pub. Date: Mar. 28, 1996

[30] Foreign Application Priority Data

Sep. 21, 1994 [NL] Netherlands ............ 9401534

[51] Int. Cl.⁶ ..................................... A61F 13/00
[52] U.S. Cl. .................. 424/422; 424/426; 424/488
[58] Field of Search ............. 424/422, 426, 424/488

[56] References Cited

U.S. PATENT DOCUMENTS 3,616,758 11/1971 Komarov ........................... 102/92
4,612,009 9/1986 Drobnik et al. .................. 424/426
4,673,438 6/1987 Wittwer ............................ 106/126
4,900,361 2/1990 Sachetto ........................... 106/213

FOREIGN PATENT DOCUMENTS

87/06129 10/1987 WIPO .
92/15285 9/1992 WIPO .
93/23012 11/1993 WIPO .

Primary Examiner—D. Gabrielle Brouillette
Attorney, Agent, or Firm—Banner & Witcoff, Ltd.

[57] ABSTRACT

The invention relates to the use of substantially fully destructurized starch for transdermal applications in humans and animals, in particular the use of solid particles such as implants. The invention further relates to the implants manufactured of substantially fully destructurized starch, in addition to methods for manufacturing the implants.

15 Claims, 1 Drawing Sheet

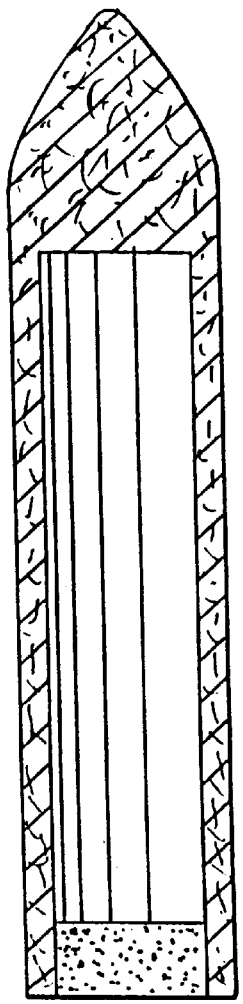
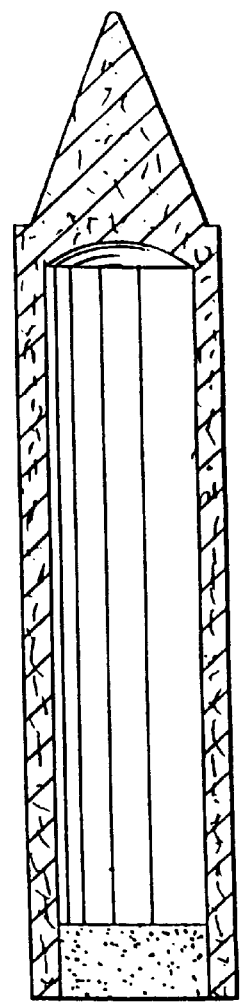
FIG. 1A
FIG. 1B
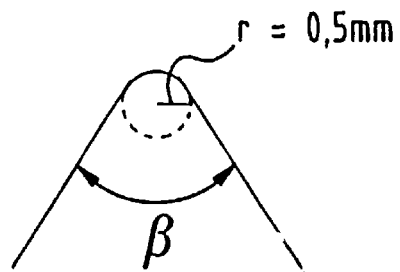
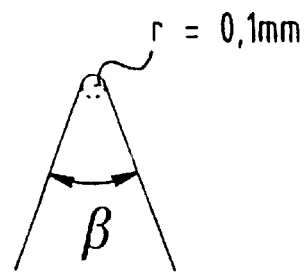
FIG. 2

USE OF STARCH FOR TRANSDERMAL APPLICATIONS

This application is a 371 of PCT/NL95/00313, filed Sep. 20, 1995.

The present invention relates to the use of starch for transdermal applications. The invention relates in particular to transdermal applications of solid products made from starch, such as implants. The invention relates more particularly to solid products produced by extruding and/or injection moulding raw materials based on starch and/or containing starch, which products are intended for transdermal applications. The invention further relates to the implants manufactured from starch, which may or may not be kinetic and may be hollow or solid.

Particular medicines, vaccines and the like may be introduced in the human or animal body in the form of implants. In order to administer implants (usually in solid form), ordinarily either a surgical incision is made through which the implant can be placed or a trocar is used, with or without mandrel.

In the first method (e.g. Endocons liquid-containing implant, as described in PCT/US93/04666), a local anaesthetic must first be given and one or more sutures made after the implant has been administered. This is a time-consuming and costly operation.

In the second method the trocar is pricked through the skin and the implant is pushed, optionally using the mandrel, into the tissues (subcutaneously/intramuscularly or in other organs). When an implant (for instance Crest-star™, Intervet, Netherlands) has to be arranged under the skin of the auricle of cattle., there is a danger of the cartilage present under the skin being damaged. Such damage increases the risk of inflammations and can adversely affect the release of the active substances. There is moreover a danger, when the animal makes an unexpected movement, of piercing right through the auricle with the trocar and even injuring the hand with which the auricle must be held. In the case a trocar with mandrel is used there is moreover a chance of damaging vulnerable implants (which contain antigens, hormones or other active substances and which are sold for instance in the form of pellets), so that the desired pattern of release is no longer certain.

In addition to by means of surgical incisions and trocars, it is also a known method to introduce implants into animals by means of ballistic biodegradable bullets such as for instance the commercially available "Biobullets" from Ballistivet or those described in U.S. Pat. No. 3,982,536, U.S. Pat. No. 3,616,758 and PCT/AU87/00091. The drawback of Ballistivet's Biobullets is their size (diameter 6.7 mm) and the fact that they contain up to 5% of the non-biologically degradable Hydroxy Propyl Cellulose (HPC). As a result, pieces of tissue have to be cut away during slaughter of the cattle treated therewith (the Biobullets are too coarse for use with other animal species or humans).

The object of the invention is to provide a transdermally applicable product, with which one or more active ingredients can be introduced into the human or animal body in simple and responsible manner.

Understood in this patent-application by "transdermal application" is any use wherein the relevant product (containing the active ingredient) is introduced into the body through the skin and/or mucous membranes. This does not therefore include uses wherein only the active ingredient enters the body. Subcutaneous, intramuscular, intrapleural, intraperitoneal and optionally intravenous administering can be envisaged here.

By "active ingredient" is meant in the broadest sense any material which must be introduced into the human or animal body. It not only comprises therapeutic, diagnostic of prophylactic compounds and compositions but also for instance identification chips and the like.

According to the invention it has now been found that products which are at least partly manufactured from substantially fully destructurized starch, particularly implants, are very suitable as vehicle for introducing active ingredients into the human or animal body in transdermal manner.

The term "substantially fully destructurized starch" means that the starch is practically fully released from the cells and granules in which it is naturally found. In practice this means that native starch is treated such that the cells and granules are disrupted as fully as possible whereby the starch is released.

It follows in fact from the literature that it is not self-evident that starch is suitable for transdermal use. Starch in native non-destructurized form has already been used for a long time for intended or unintended transdermal applications. It is thus known to administer chemically modified starch (called "Hydroxy Ethyl Starch" or "HES") in dissolved state intravenously as plasma-substitute in case of shook. To this end HES with a substitution degree of 70% is injected into the vein. The disadvantage of this product is that the starch is only partly broken down by the body. A part is excreted via the urine, another part via the bile, but a last part remains in the circulation for weeks and is then slowly deposited in the reticuloendothelial system, particularly that of the skin. This causes severe itching and pruritus (W. Jurecka et al., Arch. Dermatol. Res. 285: 13–19 (1993)).

Starch powder is further used as moisture-absorbing agent in surgical gloves. A part of this powder may wholly unintentionally enter the operation wound in specific cases. This is also a case of transdermal application of starch, albeit unintended. Once it has entered the body the starch can have adverse effects there, such as the occurrence of inflammations and granulomas when native starch granules from operating gloves enter the wound, for instance the intestines. Deutsch, M., Gynecol. Obstet. Invest. 22(2), 110–112 (1986) describes a serious peritonitis caused by such starch granules. Native starch can further give rise to sensitization of the skin (Fisher, A. A., Cutis 38(5), 307–308 (1986)) or even fistula formation (Peters, E. J. Oral Pathol. 15(8), 454–458 (1986)).

It has now therefore been found according to the invention that only when substantially fully destructurized is the starch accessible in the body to amylases, which ensure a rapid and completed gradation, whereby the undesirable side-effects of starch in the body known from the literature can be prevented.

According to the invention it has further been found that this substantially fully destructurized starch causes no toxicity phenomena such as allergy, inflammations, irritations and granuloma formation when administered (intentionally or unintentionally) transdermally. This will be further illustrated in the accompanying examples.

It had not been determined prior to the present invention that starch in substantially fully destructurized form, in contrast to native starch, is suitable to be administered transdermally as a solid product.

Substantially fully destructurized starch is per se known. It is described for instance in European patent application 282.451 and is therein designated as "destructurized starch". However, no transdermal applications are known from this publication.

The international application WO-92/15285 does however describe in a great number of examples the manufacture of different forms of medication using destructurized starch. The object of the invention described in this patent application is however to provide forms of medication with controlled release. Although a number of transdermal forms of medication is mentioned in the description and claims, not a single transdermal application is further described in the examples. Moreover, in vivo tests were not carried out with any of the mainly oral forms of medication described in the examples, whereby it is not possible to deduce the in vivo effect of such forms of medication on the basis of the description.

Substantially fully destructurized starch can be manufactured in different ways, for instance as described in EP-282.451. This publication describes a method for the destructurizing of starch by means of high temperature and/or high pressure, for instance by extruding native starch at a temperature of about 100–200° C., preferably 140–190° C., most preferably 160–185° C. at a pressure of 0 to 150 bar.

The injection moulding of substantially fully destructurized starch is also described for instance in GB-2 190 093 and EP-304.401. The pressures exerted on the starch during these injection moulding processes lie between 300 and 3000 bar, preferably between 700 and 2200 bar.

Many other destructurizing methods are of course conceivable for the object of the invention, assuming that the destructurized starch obtained meets the requirements of a rapid degradation in the body and the absence of the aforementioned undesired side-effects.

Preferably however the above mentioned extrusion/injection moulding technique is used for destructurizing starch. The advantages of extruding and injection moulding as method of destructurizing are the low cost and the methods of performing these techniques under Good Manufacturing Practice (GMP).

The use according to the invention of starch which is substantially fully destructurized has a large number of applications which will be described in further detail hereinbelow and form part of the present invention.

In one particularly advantageous embodiment of the invention the product manufactured at least partly from substantially fully destructurized starch is an implant.

Such implants can be produced by means of per se known injection moulding techniques. The starch, for instance in the form of a granulate, is processed in the injection moulding machine to the desired product. The destructurizing then also takes place in the injection moulding machine. Granulates which can serve as raw material for manufacture of the transdermal forms of medication according to the invention are for instance Commercially available. An example of a granulate is SUNPEARLS™ from AVEBE (Foxhol, Groningen, The Netherlands).

Very specific extrusion/injection moulding parameters are preferably chosen to reduce the toxicity of the starch in the end products (implants). By varying the pressure, temperature, cycle time, amount of water and the like it can be ensured that the extruded end product does not become toxic. This is further illustrated in the examples.

Implants according to the invention for instance have the shape of bullets. In veterinary medicine it is known to introduce inoculants and other transdermally administrable medication, hormones or prophylactic substances into the animal by means of kinetic implants ("bullets"). Such implants can for instance be administered with an instrument specifically designed for this purpose which is described in the Netherlands patent application 92.00844. By manufacturing such bullets according to the invention from substantially fully destructurized starch, problems such as inflammations and irritations in the animal can be avoided.

The bullets may be hollow or solid depending upon their application. Hollow bullets can be filled with the material to be administered. Solid bullets are however manufactured from destructurized starch mixed with the active ingredient. The usual additives such as albumins, gelatine, sugars, polylactic acid, copolymers with glycol acid, polyethylene glycol (PEG) etc. can be added to the starch. This usually takes place prior to the run through the injection moulding machine, for instance in order to facilitate the processing of the starch in the machine or to provide the end product with particular properties.

In principle it is possible to give the bullets any conceivable shape and size. For pigs however are recommended bullets with an outer diameter of 3 mm, a wall thickness of 0.35 mm and a length of 15 to 30 mm. For cattle can be envisaged bullets with an outer diameter of 4.5 mm, a wall thickness of 0.5 mm and a length of 45 mm. With regard to the shape a conventional bullet shape (FIG. 1A) can be envisaged but a shape with a sharp tip and a ridge (FIG. 1B) is also possible. The sharp tip ensures easy piercing of the skin, while the ridge ensures a maximum braking effect once the skin has been penetrated. As a result the injection depth can be controlled better.

The injection depth of the bullets can be influenced by different parameters. The total weight of the filled bullet, the speed imparted to the bullet, the shape of the tip and the amount of spin given thereto are therefore of importance. In this latter case applies that the more spin, the more unstable the bullet becomes when entering the tissue, whereby it will begin to tilt more quickly and will then be slowed down more quickly, whereby it penetrates less deeply. The position of the centre of gravity of the implant also determines the speed of tilting after penetration of the tissue, and thus the injection depth.

By means of a transparent tissue model of gelatine it has been found that bullets according to the invention, when they are introduced with an instrument such as described in NL-92.00844, if they should happen to fragment due to the presence of external damage, do leave fragments behind but do not cause damage to the surrounding tissue. The bullets according to the invention are therefore very safe.

The bullets do not have to be introduced with a special instrument such as described in NL-92.00844 but they can also be introduced surgically, via a needle (trocar) with mandrel or in any other manner.

BRIEF DESCRIPTION OF THE DRAWINGS

In addition, it is possible in particular applications to push specially designed bullets through the skin without any auxiliary means. Normally, trocars or injection needles are often used to introduce implants. The drawback hereof is that they generally have a very sharp tip with a radius of 0.01 mm or less and moreover possess two cutting faces. They can hereby cause damage to for instance the cartilage lying under the skin, such as in an auricle. According to the invention it has now been found that for pushing through the skin without auxiliary means the radius r of the tip of the implant is preferably smaller than 0.5 mm, more preferably smaller than 0.25 mm, most preferably between 0.03 and 0.1 mm. The radius is independent of the angle (see FIG. 2) which the tangents of the side surfaces of the tip form with each other. To make the tip as strong as possible it is recommended from a technical viewpoint to make the said angle smaller than 30°, for instance between 45° and 60°, to maximum of 120°. When technically feasible the angle may of-course also be smaller than 30°. With a thus designed implant it is possible to pierce thin skin of 0.1 to 1.5 mm thickness, depending on the type of animal. Such thin skin is for instance found on the inside and outside of the auricle or adjacently of the anus of, for instance but not exclusively, cattle, pigs, sheep and goats.

The sharpness of such bullets is not sufficient to pierce normal skin of for instance 3.0 to 3.5 mm thickness in the case of cattle, nor is cartilage damaged thereby, a danger which certainly does exist with the usual trocars. This is a great advantage, because damaged cartilage can result in inflammations. The release of active ingredients from the bullet or the implant can also be adversely affected by damaged cartilage.

The active substances and other products which can be incorporated in the hollow or solid bullets are very diverse. Herein can be envisaged medicines, antigens, sex hormones for influencing the cycle in cattle, birth inducing medication for pigs, vaccines and even identification chips.

The invention further provides a method for filling the bullets with an aqueous solution of for instance an active substance and thereafter freeze-drying the active substance, whereby it remains behind in the bullet. In principle a bullet will dissolve as soon as it is filled with water or an aqueous solution of an active ingredient. According to the invention however a method is now provided wherein the bullet is frozen for a time at for instance −20° C. and the aqueous solution of the active substance, which may or may not be in gel form, is cooled for a time to for instance 4° C. After the bullet is filled with the solution the filled bullet is frozen again for a time whereafter it is freeze-dried. In this manner the water disappears and the active substance remains behind in the bullet.

During production of the bullets various substances can be added, for instance with a anaesthetic action (such as lidocaine) or with an antiseptic action (for instance iodine) or a colorant (such as for instance methylene blue). Administering of the bullets to the animals can be made easier, respectively more pleasant with these substances.

The implants according to the present invention administered for instance using the device as described in Netherlands patent application 92.00844 are further found to have an adjuvant action. The effectiveness of a good adjuvant depends on its ability to initiate an immune response (Michel Jolivet, in "Les adjuvants, ou comment doper les vaccins et le systeme immunitaire", Biofutur, September 1989, p 45–52). It is customary to use adjuvants in vaccines, particularly in the case of those antigens which are poorly immunogenic in themselves. Adjuvants are therefore always stimulating substances, which are in principle undesirable. Examples are aluminum hydroxide, polysorbates, soapy substances like saponins (Quil A), Freunds complete or incomplete adjuvant and the like. In principle the presence of such substances in the body is always undesirable. By using a needle-free method of administering the implants according to the invention it is in principle possible to vaccinate with less or no addition of adjuvant. This results in cheaper production, fewer side effects and more predictable tissue reactions.

Starch consists of two different types of molecule, that is, amylose, the unbranched (1→4) polymer of glucose, and amylopectin, a (1→4) polymer with (1→6) branches. It has been found that during cooling amylose can group itself round free fatty acids and other polar and/or amphoteric substances such as lecithins. These groupings form crystalline structures ("resistant starch") which are not enzymatically degradable, or only slowly. According to the invention it has now been found that these "resistant starch" structures do not result in negative phenomena, such as granuloma formation etc. This is very unexpected.

However, in order to avoid amylose being able to form such crystals, an amylose-free starch, the so-called "waxy maize starch," can be chosen as raw material for the starting granulate. This enhances the general solubility and total degradability.

Experiments which have resulted in the present invention have demonstrated that the substantially fully destructurized starch is enzymatically degraded easily and quickly without toxic side effects. This will be shown in the examples.

The invention also relates to the use of substantially fully destructurized starch as additive in other products intended for transdermal application.

The present invention will be further elucidated with reference to the accompanying examples which are not intended to limit the invention in any way but are only given by way of illustration.

EXAMPLE 1

Manufacture of Substantially Fully Destructurized Starch

The substantially fully destructurized starch according to the invention, which is used in the following examples, was manufactured by extruding commercially available pure native starch, to which known bio-compatible additives such as fat and lecithin and/or polyethylene glycol and/or (water-soluble) hydrolyzed gelatine were added, at 160° C. and 150 bar according to the method described in EP-304.401 or EP-282.451. The extruded material was subsequently granulated by dividing the product leaving the extrusion device into particles of several millimeters.

EXAMPLE 2

Manufacture of Starch Implants

Bullet-shaped implants according to the invention were manufactured starting from a granulate of the starch manufactured in example 1 in the manner described in EP-304.401 or EP-282.451. Use was made herein of a so-called hot-runner mould. The implants had a conventional bullet shape with a diameter of 3 mm, a wall thickness of 0.35 mm and a length of 17 mm.

EXAMPLE 3

Cytotoxicity Test

In order to determine the cytotoxicity of the implants of example 2, the situation in the human body was imitated in a flow cell system, starting from the official ISO-protocol of ISO 10993. For this purpose a flow of a liquid tissue culture medium with a determined flow speed was created in a cell. The implants were placed in the system, whereby they gradually dissolved in the culture medium. On the outflow side of the flow cell a quantity of medium (so-called "extracts") were collected over a number of time intervals. These extracts were subsequently placed in contact with fibroblasts, whereby the influence of the extracts on the fibroblasts could be determined.

The tissue culture medium (extraction medium) was Minimal Essential Medium (MEM), to which 10% foetal calf serum was added. As blank was used an extract of this medium which had not been in contact with the implants. As positive control an extract of RIVM-positive Latex was used. The negative control was an extract of USP-negative UHMW-polyethylene.

Prior to placing in the cell the implants were sterilized for 3 hours at 50–53° C. in ethylene oxide and subsequently degassed for at least 48 hours.

A flow of 0.025 ml per hour per product was generated in the flow cell system. In the cell were placed 20 bullets manufactured from substantially fully destructurized starch. This is a total of 1 g starch. The total rate of flow therefore amounts to 0.5 ml per hour. An extraction volume of 12 ml was collected at 37° C. in each case at time intervals of 24 hours. The estimated rate of flow of tissue liquids through muscle tissue is 0.1 ml per gram tissue per minute. 6 ml per gram tissue thus passes per hour. A higher rate of flow automatically results in a more rapid freshening of the liquid and a more rapid removal of possible toxic substances. The liquid flow will consequently be greater in the body than in the flow cell used here. An extra safety margin is incorporated by selecting a rate of flow for the cytotoxicity assay which is lower than the physiological rate of flow. Concentrations which are still just toxic in the test will no longer be so in the human or animal body.

The extracts and dilutions thereof were tested for toxicity by bringing them into contact with a monolayer of human fibroblasts of the type L929, which were cultured to 80–100% confluence. After exposure to the extract the cells were examined microscopically for cytotoxic effects, such as the presence or absence of a monolayer, inhibition of cell proliferation (by means of a cell count), intracellular granulation, cellular swelling, and the percentage of cellular lysis was recorded. The results were determined in comparison with the negative control.

The results were classified as follows:
0–20% affected cells: evaluation 0, non-toxic;
20–50% affected cells: evaluation 1, slightly toxic;
50–70% affected cells: evaluation 2, mildly toxic;
70–90% affected cells: evaluation 3, moderately toxic;
90–100% affected cells: evaluation 4, very toxic;
The evaluations 0, 1 and 2 were still acceptable.
The results are shown in the table below.

TABLE 1

| Extract | Monolayer | Granulation evaluation | Growth inhibition | % Lysis | Morphology |
|---|---|---|---|---|---|
| after 72 hours | 95% | 2 | 45% | <5% | 50% coil shaped |
| 1:1 dilution | 100% | 0 | 18% | <5% | normal |
| 1:3 dilution | 100% | 0 | 20% | <5% | normal |
| 1:7 dilution | 100% | 0 | 0% | <5% | normal |
| negative control | 100% | 0 | 0% | <5% | normal |
| positive control | partial release | 4 | 95% | — | cells coil-shaped |

The above shows that the products according to the invention are not toxic.

EXAMPLE 4

Irritation Test

In this example is examined whether the implanting of bullets manufactured from substantially fully destructurized starch according to the invention causes irritations in laboratory animals.

Extracts were taken from the implants manufactured in example 2 by extracting four grams of test material for 72 hours at 50° C. with 20 ml 0.9% sodium chloride or cotton seed oil. Control solutions without the test material were prepared in similar manner.

Three healthy rabbits free of significant skin impurities were used as test animals for each pair of extracts (test and control). The animals were accommodated separately, were fed daily and had ad libitum access to water. Prior to injection the hair on the back and sides of each rabbit was cut short. Exactly 0.2 ml of the test extracts was injected intracutaneously at four separate locations on the left side of the back of each animal while 0.2 ml control solution was injected at four locations on the right side. The injection locations were examined for erythema and oedema 24, 48 and 72 hours after injection and evaluated in accordance with table 2. The average tissue reaction to the extract of the test object was compared to the control, which resulted in the irritation index.

Table 2 shows a survey of the evaluation of the intracutaneous response, and tables 3 and 4 show the results of the experiment. From these results there follows an irritation index of 0 for both the extracts with 0.9% NaCl and those with cotton seed oil. The implant according to the invention does not therefore exhibit intracutaneous toxicity.

TABLE 2

Evaluation of intracutaneous response

Erythema formation (ER):

Evaluation 0: no erythema
Evaluation 1: mild erythema
Evaluation 2: well defined erythema
Evaluation 3: moderate erythema
Evaluation 4: serious erythema to mild scab forming
Oedema formation (OE):

Evaluation 0: no oedema
Evaluation 1: mild oedema
Evaluation 2: well defined oedema
Evaluation 3: moderate oedema; about 1 mm thick
Evaluation 4: serious oedema; more than 1 mm thick

TABLE 3

Results of intracutaneous toxicity test with 0.9% sodium chloride in sterile demineralized water as extraction medium

| | | 24 hours | | 48 hours | | 72 hours | |
|---|---|---|---|---|---|---|---|
| | | ER | OE | ER | OE | ER | OE |
| | | TEST | | | | | |
| Rabbit 1 | location 1 | 0 | 0 | 0 | 0 | 0 | 0 |
| | location 2 | 0 | 0 | 0 | 0 | 0 | 0 |
| | location 3 | 0 | 0 | 0 | 0 | 0 | 0 |
| | location 4 | 0 | 0 | 0 | 0 | 0 | 0 |
| Rabbit 2 | location 1 | 0 | 0 | 0 | 0 | 0 | 0 |
| | location 2 | 0 | 0 | 0 | 0 | 0 | 0 |
| | location 3 | 0 | 0 | 0 | 0 | 0 | 0 |
| | location 4 | 0 | 0 | 0 | 0 | 0 | 0 |
| Rabbit 3 | location 1 | 0 | 0 | 0 | 0 | 0 | 0 |
| | location 2 | 0 | 0 | 0 | 0 | 0 | 0 |

TABLE 3-continued

Results of intracutaneous toxicity test with 0.9% sodium chloride in sterile demineralized water as extraction medium

|  |  | 24 hours | | 48 hours | | 72 hours | |
|---|---|---|---|---|---|---|---|
|  |  | ER | OE | ER | OE | ER | OE |
|  | location 3 | 0 | 0 | 0 | 0 | 0 | 0 |
|  | location 4 | 0 | 0 | 0 | 0 | 0 | 0 |
|  | Control | | | | | | |
| Rabbit 1 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 2 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 3 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |

TABLE 4

Results of intracutaneous toxicity test in cotton seed oil as extraction medium

|  |  | 24 hours | | 48 hours | | 72 hours | |
|---|---|---|---|---|---|---|---|
|  |  | ER | OE | ER | OE | ER | OE |
|  | TEST | | | | | | |
| Rabbit 1 | location 1 | 1 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 2 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 3 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
|  | Control | | | | | | |
| Rabbit 1 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 2 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |
| Rabbit 3 | location 1 | 0 | 0 | 0 | 0 | 0 | 0 |
|  | location 2 | 0 | 0 | 0 | 0 | 0 | 0 |
|  | location 3 | 0 | 0 | 0 | 0 | 0 | 0 |
|  | location 4 | 0 | 0 | 0 | 0 | 0 | 0 |

EXAMPLE 5

Allergy Test

In order to examine whether the implants according to the invention caused allergic reactions a sensitization test was carried out.

The implants for testing were sterilized at 50–53° C. with ethylene oxide and degassed for at least 48 hours.

A quantity of 4 grams test material was covered with 20 ml extraction medium (sodium chloride in sterile demineralized water and cotton seed oil) and extracted at 70° C. for 24 hours. The control solutions (extraction liquid without implant) were prepared in a corresponding manner.

Used as laboratory animals were albino guinea pigs of both sexes, with a weight of about 350 grams. For the testing of 1 extract 10 guinea pigs were treated with test material and 5 animals served as control group.

The guinea pigs were prepared by using electric clippers to remove the hair from an area of about 4×6 cm on the back above the dorsal capsular area at least 24 hours prior to the test. For all local applications a woven bandage of 1×2 cm was saturated with the extract for testing (or the control) and the bandage was applied to the shaven area under a sealing bandage (surgical tape) for 6 hours. The control animals were treated in similar manner with only the extraction liquids. This procedure was repeated after one and after two weeks.

14 days after the last (third) induction application all test and control animals were brought into renewed contact with the test material. For this purpose bandages saturated with test extract were applied to untested areas of each animal. After 6 hours the bandages were removed. 24 and 48 hours after removal of the bandages the animals were shaven again if necessary and the reaction was evaluated. The results are shown in table 5. Each dermal inflammation response at the test locations which was significantly greater than that observed under control conditions was considered proof of an allergic reaction. Evaluations of one or more in the test group are generally seen as an indication of sensitization provided the control animals displayed evaluations of less than 1.

The evaluation of the allergic reaction was based on the same criteria as stated in table 2. Tables 5 and 6 show the results respectively of extracts of 0.9% sodium chloride in sterile, demineralized water and cotton seed oil.

None of the tested animals displayed a significant sensitization.

TABLE 5

|  | 24 hours | | 48 hours | |
|---|---|---|---|---|
|  | ER | OE | ER | OE |
| TEST | | | | |
| Animal 1 | 0 | 0 | 0 | 0 |
| Animal 2 | 0 | 0 | 0 | 0 |
| Animal 3 | 0 | 0 | 0 | 0 |
| Animal 4 | 0 | 0 | 0 | 0 |
| Animal 5 | 0 | 0 | 0 | 0 |
| Animal 6 | 0 | 0 | 0 | 0 |
| Animal 7 | 0 | 0 | 0 | 0 |
| Animal 8 | 0 | 0 | 0 | 0 |
| Animal 9 | 0 | 0 | 0 | 0 |
| Animal 10 | | | | |
| Average test | 0 | 0 | 0 | 0 |
| Control | | | | |
| control 1 | 1 | 0 | 0 | 0 |
| control 2 | 0 | 0 | 0 | 0 |
| control 3 | 0 | 0 | 0 | 0 |
| control 4 | 0 | 0 | 0 | 0 |
| control 5 | 0 | 0 | 0 | 0 |
| control 6 | 0 | 0 | 0 | 0 |
| average control | 0.167 | 0 | 0 | 0 |

TABLE 6

|  | 24 hours | | 48 hours | |
| --- | --- | --- | --- | --- |
|  | ER | OE | ER | OE |
| TEST | | | | |
| Animal 1 | 0 | 0 | 0 | 0 |
| Animal 2 | 0 | 0 | 0 | 0 |
| Animal 3 | 0 | 0 | 0 | 0 |
| Animal 4 | 0 | 0 | 0 | 0 |
| Animal 5 | 0 | 0 | 0 | 0 |
| Animal 6 | 0 | 0 | 0 | 0 |
| Animal 7 | 0 | 0 | 0 | 0 |
| Animal 8 | 0 | 0 | 0 | 0 |
| Animal 9 | 0 | 0 | 0 | 0 |
| Animal 10 | | | | |
| Average test | 0 | 0 | 0 | 0 |
| Control | | | | |
| control 1 | 0 | 0 | 0 | 0 |
| control 2 | 0 | 0 | 0 | 0 |
| control 3 | 0 | 0 | 0 | 0 |
| control 4 | 0 | 0 | 0 | 0 |
| control 5 | 0 | 0 | 0 | 0 |
| control 6 | 0 | 0 | 0 | 0 |
| average control | 0 | 0 | 0 | 0 |

EXAMPLE 6

Implantation Test

The implant according to the invention was sterilized with ethylene oxide. HMWPE (high molecular polyethylene) strips of 1×10 mm were used as control.

The backs of 3 albino rabbits of no more than 2.5 kg were shaven. Loose hair was removed. The paravertebral muscles were subsequently anaesthetized. 4 test samples were implanted in the right-hand paravertebral muscle. 4 samples of the control plastic were implanted in the left-hand paravertebral muscle. Three days after implantation the rabbits were sacrificed and the samples and controls removed with the tissue surrounding them. The samples were embedded in paraffin or GMA, depending on the hardness of the sample material. The body reaction was quantified using light microscopic observations. The results were evaluated as shown in tables 7, 8, 9, 10. Understood by inflammation type cells are macrophages, poly-mononuclear cells, lymphocytes, eosinophil cells, plasma cells and giant cells. The results are given in tables 11 and 12.

TABLE 7

Degree of fibrosis

Evaluation 0: none observed
Evaluation 1: up to 0.5 mm
Evaluation 2: 0.5 to 1.0 mm
Evaluation 3: 1.0 to 2.0 mm
Evaluation 4: more than 2.0 mm

TABLE 8

Changes in tissue morphology

Evaluation 0: no changes
Evaluation 1: slight changes
Evaluation 2: mild changes TABLE 8-continued Changes in tissue morphology Evaluation 3: moderate changes
Evaluation 4: serious changes

TABLE 9

Presence of inflammation cells

Evaluation 0: no inflammation cells
Evaluation 1: a number of inflammation cells at contact location with sample
Evaluation 2: various inflammation cells at contact location with sample
Evaluation 3: many inflammation cells mainly at contact location with sample
Evaluation 4: many inflammation cells spread over the whole area

TABLE 10

Degree of necrosis

Evaluation 0: none
Evaluation 1: slight
Evaluation 2: mild
Evaluation 3: moderate
Evaluation 4: serious

TABLE 11

Implantation after 3 days

|  | fibrosis | tissue morphology | inflammation cells | necrosis |
| --- | --- | --- | --- | --- |
| TEST EXAMPLES | | | | |
| rabbit 1: | | | | |
| location 1 | 1 | 0 | 1 | 0 |
| location 2 | 1 | 1 | 1 | 0 |
| location 3 | 1 | 1 | 2 | 0 |
| location 4 | 1 | 1 | 1 | 0 |
| animal 2: | | | | |
| location 1 | 1 | 1 | 1 | 0 |
| location 2 | 1 | 2 | 1 | 0 |
| location 3 | 1 | 1 | 2 | 0 |
| location 4 | 1 | 1 | 1 | 0 |
| animal 3: | | | | |
| location 1 | 1 | 1 | 1 | 0 |
| location 2 | 1 | 1 | 1 | 0 |
| location 3 | 1 | 1 | 1 | 0 |
| location 4 | 1 | 1 | 1 | 0 |
| Average | 1.0 | 1.0 | 1.2 | 0.0 |
| CONTROL EXAMPLES | | | | |
| rabbit 1: | | | | |
| location 1 | 1 | 9 | 1 | 9 |
| location 2 | 1 | 0 | 1 | 0 |
| location 3 | 1 | 0 | 1 | 0 |
| location 4 | 1 | 0 | 1 | 0 |
| animal 2: | | | | |
| location 1 | 1 | 0 | 1 | 0 |
| location 2 | 1 | 0 | 1 | 0 |
| location 3 | 1 | 0 | 1 | 0 |

TABLE 11-continued

Implantation after 3 days

|  | fibrosis | tissue morphology | inflammation cells | necrosis |
|---|---|---|---|---|
| location 4 | 1 | 0 | 1 | 0 |
| animal 3: location 1 | 1 | 0 | 1 | 0 |
| location 2 | 1 | 0 | 1 | 0 |
| location 3 | 1 | 0 | 1 | 0 |
| location 4 | 1 | 0 | 1 | 0 |
| Average | 1.0 | 0.0 | 1.0 | 0.0 |

The average evaluation was 1.2, which does not represent a significant reaction.

In the same manner a bodily reaction was evaluated two weeks after implantation. The results thereof are shown in tables 12 and 13. The average body reaction evaluation was 1.0, which was likewise not significant.

TABLE 12

Implantation test after 2 weeks

|  | fibrosis | tissue morphology | inflammation cells | necrosis |
|---|---|---|---|---|
| TEST EXAMPLES | | | | |
| rabbit 1: | | | | |
| location 1 | 1 | 2 | 2 | 0 |
| location 2 | 1 | 2 | 2 | 0 |
| location 3 | 1 | 2 | 2 | 0 |
| location 4 | 1 | 2 | 2 | 0 |
| animal 2: location 1 | 1 | 0 | 1 | 0 |
| location 2 | 1 | 0 | 1 | 0 |
| location 3 | 1 | 0 | 1 | 0 |
| location 4 | 1 | 0 | 1 | 0 |
| animal 3: location 1 | 1 | 0 | 1 | 0 |
| location 2 | 1 | 0 | 1 | 0 |
| location 3 | 1 | 0 | 1 | 0 |
| location 4 | 1 | 0 | 1 | 0 |
| Average | 1.0 | 0.7 | 1.3 | 0.0 |
| CONTROL EXAMPLES | | | | |
| rabbit 1: | | | | |
| location 1 | 1 | 0 | 1 | 0 |
| location 2 | 1 | 0 | 1 | 0 |
| location 3 | 1 | 0 | 1 | 0 |
| location 4 | 1 | 0 | 1 | 9 |
| animal 2: location 1 | 1 | 0 | 1 | 0 |
| location 2 | 1 | 0 | 1 | 0 |
| location 3 | 1 | 0 | 1 | 0 |
| location 4 | 1 | 0 | 1 | 0 |
| animal 3: location 1 | 1 | 0 | 1 | 0 |
| location 2 | 1 | 0 | 1 | 0 |
| location 3 | 1 | 0 | 1 | 0 |
| location 4 | 1 | 0 | 1 | 0 |
| Average | 1.0 | 0.0 | 1.0 | 0.0 |

EXAMPLE 7

Amylase Assay

The implants according to the invention are manufactured of starch which is broken down quickly in the body. This example shows that a rapid induction of the starch-degrading enzyme amylase takes place. The amylase activity was determined in pig tissue after implantation of the implants according to the invention and in untreated tissue as control. Tissue extracts of tissue homogenates were prepared in salt solution and quantified for amylase activity.

Tissue extracts were prepared at a temperature between 0° and 10° C. From three tissue samples and three controls a gram was cut into slices and stored on ice. The tissue slices and 5 ml 0.9% sodium chloride solution were mixed in a 10 ml tube of a Waring blender for 3 minutes at 20,000 RPM. During this procedure the tube was cooled with an ice water mixture. The resulting suspension was collected in a clean tube. The blender tube and the knife were washed with 4 ml salt solution which was also added to the suspension whereby the final volume became 10 ml. Finally, the suspension was centrifuged for 12 minutes at 4° C. and 1100 RCF and the supernatant kept at −80° C. The assays of this tissue extract were performed on 1 to 10 diluted concentrations of tissue liquid components.

The amylase activity was determined according to Sigma procedure no. 700. The procedure makes use of a colour reaction between starch and iodine which produces an intense blue colour, while the oligosaccharides produce a red colour as according to the diagram below.

starch $\xrightarrow{\text{Amylase}}$ oligosaccharides $\xrightarrow{\text{Amylase}}$ maltose and
(blue (red with iodine) glucose
with
iodine)

The colour change from blue to red-brown was sufficiently pronounced to make a visual detection of the end point possible without the use of a spectrophotometer. The end point was determined by removing parts of the serum starch reaction mixture at predetermined intervals and adding thereto to an iodine solution. As long as starch is present a purplish colour develops. During the course of the incubation the colour changes from blue to blue-purple to red-purple and eventually to red-brown. This is the end point. The result is evaluated as follows:

0=no colour change; purplish

1=colour change; red-purple

2=end point; red-brown

The amylase activity in the sample is calculated by means of the formula:

$$\text{amylase activity} = \frac{1800 * 10}{\text{incubation time (end point)}} U/dl$$

The results are shown in table 13.

TABLE 13

| Incubation time (min) | A | A | A | A 1:5 | A 1:10 | B | B | B | B 1:5 | B 1:10 |
|---|---|---|---|---|---|---|---|---|---|---|
| 2 | 0 | 0 | 0 | 0 | 0 | 0 | 0 | 0 | 0 | 0 |
| 4 | 0 | 0 | 1 | 0 | 0 | 0 | 0 | 0 | 0 | 0 |
| 6 | 1 | 1 | 2 | 0 | 0 | 0 | 0 | 0 | 0 | 0 |
| 8 | 2 | 2 | 2 | 0 | 0 | 0 | 0 | 0 | 0 | 0 |
| 10 | 2 | 2 | 2 | 0 | 0 | 0 | 0 | 1 | 0 | 0 |
| 12 | 2 | 2 | | 0 | 0 | 1 | 1 | 2 | 0 | 0 |
| 15 | | | | 0 | 0 | 2 | 2 | 2 | 0 | 0 |
| 18 | | | | 0 | 0 | 2 | 2 | 2 | 0 | 0 |
| 23 | | | | 1 | 0 | 2 | 2 | | 0 | 0 |
| 28 | | | | 2 | 0 | | | | 0 | 0 |
| 32 | | | | 2 | 0 | | | | 0 | 0 |
| 36 | | | | 2 | 0 | | | | 0 | 0 |
| 44 | | | | | 0 | | | | 0 | 0 |
| 50 | | | | | 0 | | | | 0 | 0 |
| 56 | | | | | 0 | | | | 1 | 0 |
| 62 | | | | | 1 | | | | 1 | 0 |
| 70 | | | | | 1 | | | | 2 | 0 |
| 80 | | | | | 2 | | | | 2 | 0 |
| 90 | | | | | 2 | | | | 2 | 0 |
| 100 | | | | | 2 | | | | | 0 |
| 110 | | | | | | | | | | 1 |
| 120 | | | | | | | | | | 2 |
| Amylase/sample (U/dl) | 2250 | 2250 | 3000 | 3200 | 2600 | 1200 | 1200 | 1500 | 1500 | 1500 |
| Average/sample | | | 2660 U/dl | | | | | 1380 U/dl | | |

Normal serum levels of amylase activity in humans vary between 50 and 200 U/dl. The recorded results demonstrate that the test is sensitive to pig amylase and that normal tissue values (controls) are at least 10 times as high as normal human serum values. The data likewise indicates that the amylase activity in pig tissue treated with starch is at least times as high as in normal human serum. The result provides no information about the localization of the amylase, or whether it is intra- or extracellular and whether this is a local or systemic reaction. The conclusion is that implantation of starch implants in pig tissue causes a reaction characterized by an increased amylase activity in the tissue.

EXAMPLE 8

Tissue Reactions to Implantation of the Implant According to the Invention in the Pig In this experiment a pig receives implants at different times which are introduced using the instrument described in the Netherlands patent application 92.00844.

A pig of about 65 kg received a first series of implants in the left side of its body on day 1. Just before introduction the implants were sterilized in 70% alcohol for several seconds and dried in the air. For injection the tip of the barrel of the aforementioned instrument was held about 1 cm from the skin, wherein the longitudinal axis was positioned as perpendicularly of the skin as possible. The injections 1 and 2 were given successively in the neck, injections 3, 4 and 5 in the musculus longissimus dorsi and the injections 6, 7 and 8 one below another in the buttock. The injection locations were disinfected using gentian violet spray with chlortetracycline therein. After 18 days the whole procedure was repeated on the right side of the pig. Three days later, on day 21, the pig was sacrificed by means of an injection of 50 cc euthesate in the vena cava cranialis. The injection locations were shaven and evaluated.

Very small scars were observed in the skin on the left side (after 21 days). On the right side no swellings were visible but there were very slight, small wounds with a small blood scab. Mild redness was only observed at the eighth injection.

During dissection it was found that the injections 1 and 2 on the left side left no trace whatever, subcutaneous or intramuscular. Injections 3 and 4 are also no longer discernible subcutaneously, but intramuscularly an elongate connective tissue strand of several centimeters length and less than one millimeter thickness is visible. Of the injections 5 to 8 on the left side no trace could be found.

The injections on the right side (3 days) displayed at a depth of 2 cm a slight reaction with a cross-section of 1 cm wherein no swelling was observed but only a small dark discolouring. Injection 3 displayed subcutaneously very light bleeding and mild oedema. At injection 4 nothing was discernable subcutaneously while at 3 cm depth intramuscularly small bleeding with calcification granules was observed. The results of injection 5 corresponded with those of injection 3, while for the injections 6, 7 and 8 small bleedings were observed subcutaneously and intramuscularly along the bullet passage to a depth of 5–6 cm.

On the microscopic coupes can be seen that three days after implantation a degeneration of still vital muscle tissue occurs, in addition to small temporary calcifications, very small bleeding caused by capillary vessels which are torn by the projectile as it shoots past, necrotic material which is not vital and is probably crushed by the projectile as it passes, and cellular clearing reactions indicated by the presence of lymphocytes, polymononuclear cells and-macrophages. Because the tissue destruction is very minimal there need be no fear of puss and/or fistula formation and after a few weeks the clearing reactions will only leave a slight scar formation.

EXAMPLE 9

In Vivo Injection Test

In this experiment is determined whether the animals display abnormal activity or appear to have a pain sensation. It is also determined what the effect of the injection is on the skin.

Seven male pigs with an average weight of 53 kg. were injected on day 1, 20, 38, 62 (2×) and 67 with an implant according to the invention using the instrument as described in NL 92.00844.

For 7 days, following every injection and particularly after the first hour and after 6 to 7 hours, a record was kept of all pigs as to whether the animals displayed abnormal activities or gave the impression of being in pain. The injection locations were checked for bleeding, swelling, painfulness, redness or exudate after 1 hour, 6 to 7 hours, 1, 2, 3, 4, 5, 6 and 7 days. On day 81 the animals were sacrificed and it was visually determined whether the injections had left any trace.

From this experiment it was found that the administering of the implants had no noticeable effect on the animals. Some animals displayed a mild swelling of the skin at the position of the injection but after 3 to 4 days these phenomena had completely disappeared. After 81 days no trace whatever of the total of 42 administered implants was found, nor were any scars observed which could have been caused by the implants. It can be concluded therefore that administering of the implants has no adverse effect whatever on the animals.

EXAMPLE 10

The Relation Between Cytotoxicity and Processing

It was noted that, during injection moulding of the starch, products which stayed longer in the injection moulding machine had a browner colour than other products. The brown colouring could be an indication of cytotoxicity. In this example quantitative data are collected relating to the cytotoxic effects of the test material on a fibroblast monolayer.

Four groups of samples were used. Their processing time in the machine was linked to their brown colouring. The The classification of the samples A, B, C and D was further based on optical density (OD), which was determined using a Kinetic Reader spectrophotometer (Biotek, model EL 312E). The optical density was measured at 380 nm and 405 nm. The samples were cut into pieces of several millimeters in length in order to obtain cylinders which were laid on the bottom of a 96-well microtitre plate. The plate is placed in the spectrophotometer. Table 16 shows the results.

The cytotoxicity was tested on the basis of a procedure according to the ISO 10993-5 and USP XXII standards.

The samples were sterilized with ethanol and deaerated for more than 48 hours prior to the test. All procedures were performed under sterile conditions.

Extracts were prepared by extracting quantities of test material and control material with an outer surface area of 60 $cm^2$ for 24 hours at 37° C. in 20 ml minimal essential medium (MEM, tissue culture medium supplemented with 10% foetal calf serum). USP neg. UHMW (Ultra High Molecular Weight) polyethylene was used as negative control. The positive control was an RIVM-pos. Latex.

In summary, the procedure was as follows: a monolayer of human skin fibroblasts (PK*$) was cultured to 80–100% confluence and brought into contact with an extract of the test material (n=3), the negative control material (n=3) or the positive control (n=1). After 24 hours of exposure to the extract at 37° C. the cell were examined and the cytotoxic effects were determined microscopically by evaluation of:

a=interruption of the monolayer b=degree of cellular lysis c=change in cell morphology The scores for a, b and c were corrected for the negative control, which results in the microscopic average. By treating the wells which were used for a, b and c, with trypsin the cells were suspended, whereafter they were counted microscopically with a Burker chamber. In this manner the inhibition of the cell proliferation (d) after 24 hours was determined. A correction was made for the negative control.

The different observations were classified as shown in the following table 14.

TABLE 14

| | disruption of the monolayer ML | degree of cellular lysis CL | changes in cell morphology CM | inhibition cell growth CG |
| --- | --- | --- | --- | --- |
| class 0 | none observed | none observed | no changes, normal cells | 0–10% |
| class 1 | slight | 0–5% | slight changes, some cells affected | 10–30% |
| class 2 | mild | 5–10% | mild changes, some cells round and/or coil shaped | 30–50% |
| class 3 | moderate | 10–20% | moderate changes many cells round and/or coil shaped | 50–70% |
| class 4 | serious | >20% | serious changes, roughly all cells show morphological changes | 70–100% | samples A, B and C represent three groups with an increase in brown coloration clearly discernible with the naked eye. A lubricant was necessary to enable removal of these products from the mould. Sample D showed the least brown coloration, was produced in a sequential series and required no lubricant.

Acceptance criteria are shown in table 15.

TABLE 15

| cytotoxic response | cytotoxic effect | sufficient/insufficient |
|---|---|---|
| 0–1 | not toxic | sufficient |
| 1–3 | slightly toxic | sufficient |
| 3–5 | mildly toxic | test again |
| 5–7 | moderately toxic | insufficient |
| 7–8 | very toxic | insufficient |

Table 16 shows the compilation of the test results.

TABLE 16

| Sample | $OD_{380}$ | $OD_{405}$ | total cytotoxic response |
|---|---|---|---|
| A | 0.529 | 0.373 | 2.4 sufficient |
| B | 0.823 | 0.783 | 5.2 insufficient |
| C | 1.189 | 0.973 | 7.0 insufficient |
| D | 0.610 | 0.640 | 2.6 sufficient |
| background | 0.060 | 0.042 | |

The test shows a clear positive linear correlation between the brown colouring and the cytotoxicity of the material. The use of lubricant has no effect on the total cytotoxicity response.

EXAMPLE 11

The Administering of an Implant by Means of Pushing

An implant according to the invention manufactured from starch which is destructurized according to example 1 with a length of 17.5 mm, a diameter of 3.00 mm, a radius of the tip of 0.25 mm and an angle between the tangent lines of the side walls of the tip of 60° was administered subcutaneously to a piglet and a calf. The implant was pushed into the auricle. The four signs of inflammation, redness, swelling, warmth and pain were not observed. Nor was any bleeding seen.

When an empty implant was introduced the cylindrical part had disappeared within two hours, while the solid tip could no longer be seen after 5 hours. The sharp tip was no longer sharp after a few seconds, whereby there was no danger of the skin being pierced from inside.

EXAMPLE 12

Adjuvant Action of the Implants

In order to test whether the implants according to the invention have any effect in the administering of vaccinating substances, the model inoculant bovine serum albumin (BSA) was administered in three different ways.

The first series of bullets contained a water-in-fat emulsion (with Tween™ and Spans™) as adjuvant. The watery phase contained 500 μg BSA as antigen. The second series of bullets each contained a dry pellet with a diameter of 2 mm, consisting of a carrier substance (sugar) and 500 μg BSA. The third series of bullets was prepared according to the above described freezing method. Placed into each of these bullets was a watery solution with 500 μg BA which remained behind as powder in the bullets after freeze-drying. The bullets were sealed with a droplet of fat.

The bullets with the known adjuvant were not found to give a statistically significantly higher immunological response than the bullets to which no adjuvant was added. It follows herefrom that the bullets themselves also have an adjuvant action.

I claim:

1. A transdermal implant comprising substantially fully destructurized starch wherein the implant is a bullet.

2. The transdermal implant as claimed in claim 1 wherein the is hollow.

3. The transdermal implant as claimed in claim 2 wherein the bullet further comprises a filling comprising at least one therapeutic, diagnostic or prophylactic compound and optionally a suitable diluent.

4. The transdermal implant as claimed in claim 1 wherein the bullet is solid.

5. The transdermal implant as claimed in claim 4 wherein the bullet comprises a mixture of substantially destructurized starch and at least one therapeutic, diagnostic or prophylactic compound.

6. The transdermal implant as claimed in claim 1 wherein the implant comprises a tip such that manual pushing of the implant through skin is possible.

7. The transdermal implant as claimed in claim 6 wherein the radius r of the tip of the implant is smaller than 0.5 mm, and the angle which the tangent lines of the side surfaces of the tip form with each other is not smaller than 30° and up to a maximum of 120° in order to enable pushing of the implant through skin of 0.1 to 1.5 mm thickness.

8. The transdermal implant as claimed in claim 7 wherein the radius r of the tip of the implant is smaller than 0.25 mm and the angle which the tangent lines of the side surfaces of the tip form with each other is between 45° and 60°.

9. The transdermal implant as claimed in claim 8, wherein the radius r of the tip of the implant is between 0.03 and 0.1 mm.

10. The transdermal implant as claimed in claim 8 wherein the filling comprises an inoculant.

11. The transdermal implant as claimed in claim 2 wherein the bullet contains an identification chip.

12. The transdermal implant as claimed in claim 3 wherein the filling comprises a therapeutic or prophylactic composition.

13. A method of administering an implant transdermally comprising introducing the transdermal implant of claim 1 under the skin.

14. The method of claim 13 wherein the transdermal implant comprises substantially fully destructurized starch and at least one therapeutic, diagnostic or prophylactic compound, optionally in combination with a suitable diluent.

15. A method for filling a hollow bullet transdermal implant with a therapeutic, diagnostic or prophylactic compound comprising freezing the implant, cooling a watery solution containing the therapeutic, diagnostic or prophylactic compound, pouring the watery solution into the implant, freezing the filled implant, and freeze drying the filled and frozen implant.

* * * * *